(12) United States Patent
Wharton

(10) Patent No.: US 6,691,351 B1
(45) Date of Patent: Feb. 17, 2004

(54) BODY IMMOBILIZING HARNESS FOR SPINE PROTECTIVE CARRIERS

(76) Inventor: Jarrett Wharton, 4524 Birchman, Fort Worth, TX (US) 76107

( * ) Notice: Subject to any disclaimer, the term of this patent is extended or adjusted under 35 U.S.C. 154(b) by 0 days.

(21) Appl. No.: 10/216,595

(22) Filed: Aug. 9, 2002

(51) Int. Cl.[7] .............................................. A61G 1/044
(52) U.S. Cl. .............................. 5/628; 5/625; 128/870; 128/875
(58) Field of Search ...................... 5/625, 628; 128/870, 128/875, 876

(56) References Cited

U.S. PATENT DOCUMENTS

| | | | | |
|---|---|---|---|---|
| 2,972,755 A | * | 2/1961 | Abel .............................. | 5/628 |
| 3,601,824 A | * | 8/1971 | Bradford ........................ | 5/628 |
| 4,794,656 A | | 1/1989 | Henley, Jr. | |
| 4,841,961 A | * | 6/1989 | Burlage et al. ............... | 128/876 |
| 5,014,374 A | * | 5/1991 | Williams ....................... | 5/628 |
| 5,083,574 A | * | 1/1992 | Schlutow ....................... | 5/628 |
| 5,211,186 A | * | 5/1993 | Shoemaker et al. ............ | 5/628 |
| 5,435,323 A | | 7/1995 | Rudy | |
| 6,092,525 A | * | 7/2000 | Church ......................... | 128/869 |
| 6,135,115 A | * | 10/2000 | Rodarte ........................ | 128/869 |
| 6,363,936 B1 | * | 4/2002 | McCormick et al. ........ | 128/870 |

* cited by examiner

Primary Examiner—Michael F. Trettel

(57) ABSTRACT

A spine protecting strap apparatus for trauma victim transportation has a longitudinal zipper with each side configured for detachable connection to the edges and at the head end of the supporting carrier. A plurality of adjustable length, transverse strap assemblies with releasable, slack take-ups have one end permanently connected to either side of the longitudinal zipper and the opposite end configured for detachable connection to corresponding edges of the carrier, so that, with the longitudinal zipper fully closed and the detachable connections connected to the carrier, the transverse straps are effectively connected across the width of the carrier and the straps can be tightened in order to immobilize the victim's body for transportation.

9 Claims, 2 Drawing Sheets

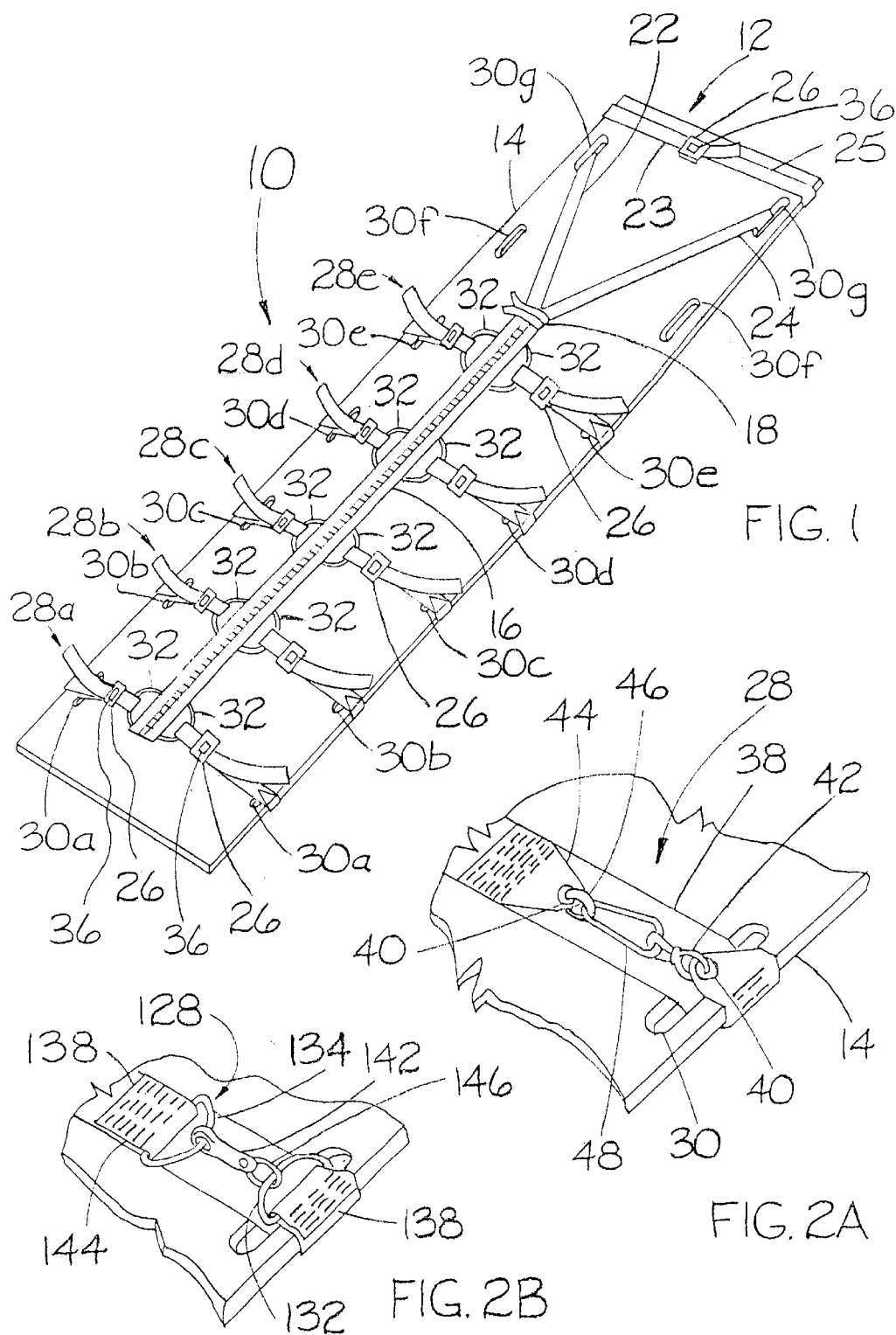

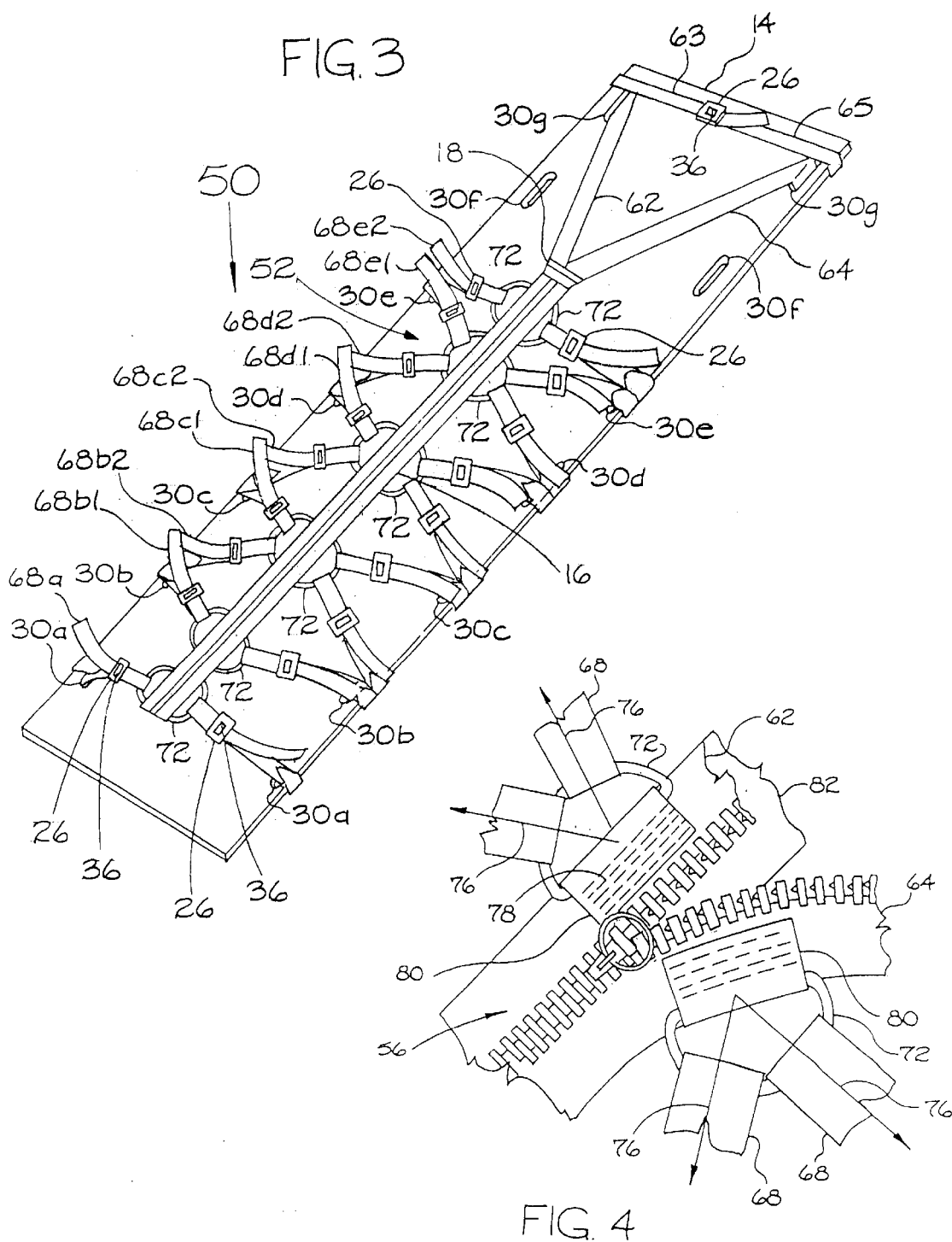

BODY IMMOBILIZING HARNESS FOR SPINE PROTECTIVE CARRIERS

TECHNICAL FIELD

The present invention relates to the field of medical equipment for patient handling, and more particularly to spine protective carriers for emergency patient transportation.

BACKGROUND

Emergency transportation of trauma victims is fraught with problems. There are often severe, life threatening injuries and transportation adds yet another degree of risk for the victim. The injured party may be carried to the ambulance on a wheeled gurney or rescue teams may use stretchers, backboards or Stokes baskets as carriers to move victims from the trauma. The terrain may be steep and treacherous, sometimes so bad that the victim must be dragged or hoisted out by a cable lift. If back and neck injuries are involved, the carrier must be equipped with a means to immobilize the victim to prevent further nerve damage. Typically, immobilization is achieved by the use of restraining straps that run across the victim's body and are connected at the edges of the carrier. Since any failure could have dire consequences, such strapping devices must be designed and made to high standards of strength and durability.

Various strap arrangements have been offered for use with carriers, some using cam-lock slide connectors, and some using VELCRO hook and loop fasteners or other slack take-up devices. These devices are in the form of assemblies of straps and connectors that can be procured and fastened to any carrier. State-of-the-art strap restraint systems require all of the lateral straps to be disconnected to receive a body onto the carrier. Then each lateral strap must be reconnected separately. Inasmuch as this is done under adverse conditions and the straps must be connected and tightened quickly, the number of straps is kept to the minimum required for effective immobilization. In general, these devices serve the intended purpose of immobilizing an injured person for transit.

The greatest need for advancement in this art is always to reduce the time and effort needed for stowage, deployment and application. A device comprising a plurality of straps, loose at one end, is likely to become tangled and difficult to apply. This is especially true if the assembly becomes separated from the carrier. Burlage et al., U.S. Pat. No. 4,841,961 for instance, teaches color-coding the straps as an aide to right-side-up orientation.

A first object of the present inventions is therefore, to provide a body immobilizing strap arrangement that can be operatively attached to existing carriers, without modification. A second object is to provide such a strap arrangement in a form that can be fitted to a patient's body, without need for disconnecting and reconnecting individual strap members. A third object is to provide a sufficient selection of straps to fit a patient's body, regardless of size, without compromised immobilization. A fourth object is to provide a strap arrangement that can be used quickly and reliably, regardless of ambient conditions. Yet another object is that the strapping arrangement be resistant to disarray when stowed or being prepared for use.

SUMMARY OF THE INVENTION

The present inventions pertain to a body immobilizing harness used for emergency trauma victim transportation on a carrier. These inventions relate to or employ some steps and apparatus well known in the emergency medical equipment arts and therefore, not the subject of detailed discussion herein. These harness assemblies are used in circumstances when quick action may prevent death or permanent injury. For that reason, we find state-of-the-art immobilizing harnesses design is focused on minimizing the number of straps and connections needed to hold a body in place. This also serves to minimize the strap-tangling problem, so the harness will be ready for use when the carrier is taken out for use.

In the present inventions, each side of a longitudinal zipper assembly is configured for detachable connection at the head end edges of a carrier. A plurality of adjustable length, transverse strap assemblies are provided, with one end permanently connected to either side of the longitudinal zipper and the opposite end configured for detachable connection to the corresponding edge of the carrier. These transverse strap assemblies may be perpendicular to the longitudinal zipper or at a diagonal angle. A typical industrial class zipper assembly has a separating strength of 200 pounds per linear inch. This level of strength is sufficient to allow direct connection of the straps to the zipper side members and the size of the interlocking elements is such as to resist damage. Even so, as a conservative design measure, the use of "D" ring connectors distributes strap tension forces over approximately 3" of zipper length. "D" ring connections also mitigate any "peeling" load concentrations. Quick releasable, cam locking slack take-up devices, well known in the art, are operatively included for tightening each transverse strap assembly on the victim's body.

With the longitudinal zipper fully closed, the detachable connections of the body immobilizing harness are connected to the carrier as described above. The assembly is stowed, preferably with the transverse straps slack rather than tightened. To transport a victim, the zipper is opened, so that the straps can be laid to either side of the carrier. For smaller victims, the lowermost straps may be loosened enough that it is not even necessary to disengage the lower end connection of the zipper. After the victim is maneuvered onto the carrier, the zipper is closed to reconnect the transverse straps across the victim's body for tightening as appropriate. Thus, there is never more than the one zipper connection to be made at the emergency site. In any event, the pin and socket elements of the starting connection for industrial class zippers are large and easily manipulated.

The inherently organized strap arrangement of the present inventions has the unobvious advantage of allowing the use of a greater number of transverse, lateral or diagonal straps, without tangling when stowed or risking lost time in making connections when time is critical and conditions are adverse.

BRIEF DESCRIPTION OF THE DRAWINGS

The accompanying drawings are incorporated into the specification to assist in explaining the present inventions. The drawings illustrate preferred and alternative examples of how the inventions can be made and used and are not to be construed as limiting the inventions to only those examples illustrated and described. The various advantages and features of the present inventions will be apparent from a consideration of the drawings in which:

FIG. 1 is a perspective view of a preferred embodiment of the present inventions;

FIG. 2A is a perspective view of a construction detail of FIG. 1, showing attachment of a strap to the carrier;

FIG. 2B is a perspective view of an alternative strap attachment to a carrier;

FIG. 3 is a perspective view of an alternative preferred embodiment of the present inventions; and FIG. 4 shows the zipper assembly of FIGS. 1 and 2.

DETAILED DESCRIPTION OF THE DRAWINGS

The present inventions are described in the following by referring to drawings of examples of how the inventions can be made and used. In these drawings, reference characters are used throughout the views to indicate like or corresponding parts. The embodiments shown and described herein are exemplary. Many details are well known in the art, and as such are neither shown nor described.

FIG. 1 shows a preferred embodiment 10 of the present inventions, wherein backboard 14 is shown as being representative of stretchers, Stokes baskets and other trauma victim carriers. Immobilizing harness assembly 12, having a head end and a foot end, is connected to backboard 14, as when stowed and ready for use. Attachment points for immobilizing harness assembly 12 are provided by hand holes 30a–g spaced along each longitudinal edge of backboard 14. Central, longitudinal zipper 16 comprises right and left hand sides, 22 and 24 respectively, are longitudinal members, central to the present inventions. Upper ends 23 and 25 of longitudinal members 22 and 24 diverge and are passed through the respective hand holes 30g. Cam locking buckle 26, with release button 36, is permanently connected to upper end 25 to receive upper end 23 at the head end. Connected in this manner, it should never be necessary to disconnect upper end 23 from upper end 25. As an alternative preferred embodiment, upper ends 23 and 25 may be connected to backboard 14 at hand holes 30g, in the manner discussed for body straps 28 here below. As with body straps 28, both upper ends 23 and 25 then include a cam locking buckle 34. Either way, upper ends 23 and 25 function as a pair of adjustable shoulder straps that can be tightened, as required. Permanently attached to either longitudinal member 22 or 24 is tie strap 18, which is wrapped around both members where they diverge as the first step in immobilizing a subject. Tie strap 18 holds longitudinal members 22 and 24 together, so as to eliminate the parting force at the end of the zipper.

Opposed pairs of identical left and right lateral hand body strap assemblies 28a–e are attached to backboard 14 through hand holes 30a–e, where they are secured, as discussed below. Right and left body strap assemblies 28a–e connect to right and left longitudinal members 22 and 24 respectively, through "D" rings 32. A typical, industrial class part having a separating strength of 200 pounds per linear inch is used for longitudinal zipper assembly 16. Such strength is sufficient to allow direct connection of lateral right and left body strap assemblies 28a–e to side members 22 and 24. Even so, in the interest of conservative design practices, "D" ring connectors 32 are provided to distribute the pulling force of body strap assemblies 28a–e over at least 3" of zipper length. These "D" ring connectors 32 also mitigate "peeling" load concentrations, a benefit more fully apparent in the diagonal body strap embodiment of FIG. 3.

Releasable, cam locking slack take-up buckles 26, as used in some seat belts and well known in the art, are operatively included in each body strap assembly 28a–e. Buckles 26 are preferred for this application, because the selected body strap 28a–e, or shoulder strap 22/24, is tightened simply by pulling on the respective strap end and is released by pressing central release button 36. Although the ends of strap assemblies 28 are shown to be pulled outwardly from the body of the victim, the assemblies can be reconfigured, within the scope of the invention, to reverse the direction of pull.

FIG. 2A shows a manner of attaching typical body strap assembly 28 to backboard 14. The end of webbing 38 is doubled over and saturated with either a thermosetting, high strength plastic or an epoxy. After setting, the end is trimmed to shape and grommet 40 is installed for wear resistance and strength. Snap hook 42 is fitted through grommet 40. Webbing flap 44 is made in a similar manner and sewn to webbing 38 to provide an anchor for spiral ring 46 and loop 48. Then snap hook 42 is passed through hand hole 30, as shown, and hooked to loop 48. In this manner, a detachable connection is made to backboard 14, a connection allowing angular freedom for either lateral or diagonal strap orientation. While the aforesaid arrangement provides a viable detachable connection for body strap assemblies 28 to backboard 14, it represents only one possible arrangement. Another apparatus for achieving such a connection would be provided by an enlarged version of spiral ring 46, passing through grommet 40 at the reinforced end of webbing 38, around the edge of backboard 14 and through a hand hole 30.

FIG. 2B shows an alternative manner of attaching typical body strap assembly 128 to backboard 14. The end of webbing 138 is doubled over "D" ring 132 where it is stitched securely in place and snap hook 142 is attached by means of spiral ring 146. Webbing loop 144 is made in a similar manner, in being doubled over and sewn to webbing 138 to provide an anchor for "D" ring 134. Then, snap hook 142 is passed through hand hole 30, as previously shown, and hooked to "D" ring 134. In this manner, a detachable connection is made to backboard 14, a connection allowing angular freedom for either lateral or diagonal strap orientation. While the aforesaid arrangement provides another detachable connection for body strap assemblies 128 to backboard 14, it represents only one possible alternative arrangement.

FIG. 3 shows alternative preferred embodiment 50 of the present inventions, wherein immobilizing harness assembly 52 is connected to backboard 14 as it would be configured when stowed or ready for use. Attachment points for immobilizing harness assembly 52 are provided by a series of hand holes 30a–g along each longitudinal edge of backboard 14. Central, longitudinal zipper 56 comprises right and left hand sides, which act as longitudinal members, 62 and 64 respectively. The upper ends 63 and 65 of longitudinal members 62 and 64 diverge, and pass through upper end hand holes 30g, to be connected by cam locking take-up buckle 26. In this manner, longitudinal members 62 and 64 function as a pair of adjustable length shoulder straps that can be tightened as required.

Identical left and right, lateral and diagonal body strap assemblies in pairs 68a, 68b1, 68b2, 68c1, 68c2, 68d1, 68d2, 68e1 and 68e2 are attached to backboard 14 through hand holes 30a–e, where they are secured in the manner discussed above. Right and left body strap assemblies 68 connect to right and left longitudinal members 62 and 64 respectively, through symmetrically located "D" rings 72. Releasable, cam locking slack take-up buckles 26, with release buttons 36, are operatively included in each body strap assembly 68.

The industrial class part used for longitudinal zipper assembly 56 has a separating strength of 200 pounds per linear inch. Such strength is sufficient to allow direct connection of lateral and diagonal body strap assemblies 68 to side members 62 and 64. Even so, as a conservative design practice, "D" ring connectors 72 are provided to distribute the pulling force of body strap assemblies 68 over approximately 3" of zipper length when tightened to bind and immobilize a victim's body. "D" rings 72 also eliminate "peeling" load concentrations by directing strap force vectors 76 generally to the centers of aligned "D" ring attachment areas 78 (ref. FIG. 4).

FIG. 4 shows the assembly of longitudinal zipper 16 in greater detail. Here it is shown how "D" rings 72 attach to longitudinal members 62 and 64 by sewn-on attachment loops 80, and how body strap force vectors 76 are directed generally to the centers of attachment areas 78. Also of note in this view, is the plastic shield 82 underlying longitudinal zipper 56, so as to prevent interference to zipper closure by the victim's clothes.

The embodiments shown and described above are exemplary. It is not claimed that all of the details, parts, elements, or steps described and shown were invented herein. Even though many characteristics and advantages of the present inventions have been described in the drawings and accompanying text, the description is illustrative only. Changes may be made in the detail, especially in matters of shape, size, and arrangement of the parts within the scope and principles of the inventions. The restrictive description and drawings of the specific examples above do not point out what an infringement of this patent would be, but are to provide at least one explanation of how to use and make the inventions. The limits of the inventions and the bounds of the patent protection are measured by and defined in the following claims.

I claim:

1. Strapping apparatus for immobilizing the body of a subject on a supporting substantially flat carrier, comprising:
    a longitudinal sliding connector having incrementally separable and joinable right and left longitudinal members, with head and foot ends;
    a first plurality of body binding strap assemblies having first and second ends, the first ends permanently connected at spaced intervals to the right hand longitudinal member, and the second ends configured for detachable connection to the substantially flat carrier;
    a second plurality of body binding strap assemblies having first and second ends, the first ends permanently connected at spaced intervals to the left hand longitudinal member, and the second ends configured for detachable connection to the supporting carrier; and
    a releasable cam locking slack take-up device operatively included in each body binding strap assembly, between the first and second ends thereof.

2. Strapping apparatus according to claim 1, wherein the head end right and left body binding strap assemblies are configured for detachable connection proximate respective flat carrier head end corners.

3. Strapping apparatus according to claim 1, wherein the right and left longitudinal member head ends are configured for spaced apart, detachable connection proximate respective flat carrier head end corners.

4. Strapping apparatus according to claim 1 wherein the detachable connections are snap hooks.

5. Strapping apparatus according to claim 1 wherein the detachable connections are hook and loop connectors.

6. Strapping apparatus according to claim 1 wherein the detachable connections are spiral ring connectors.

7. Strapping apparatus according to claim 1, wherein adjacent body binding strap assemblies are connected to the right and left longitudinal members proximate a common point.

8. Strapping apparatus according to claim 1, wherein the body binding strap assemblies are connected to the right and left longitudinal members by "D" rings.

9. The method for immobilizing the body of a subject on a supporting flat carrier, comprising the steps of:
    providing a longitudinal zipper;
    connecting either side of the zipper to the flat carrier with a plurality of adjustable length straps;
    opening the zipper and placing the sides thereof, with the connected straps to the side of the supporting carrier;
    placing the body of the subject on the supporting carrier;
    closing the zipper; and
    tightening the strap length adjustment, so as to immobilize the body.

* * * * *